United States Patent
Vardi et al.

(10) Patent No.: US 8,926,519 B2
(45) Date of Patent: *Jan. 6, 2015

(54) OPITCAL-ACOUSTIC IMAGING DEVICE

(75) Inventors: Gil M. Vardi, Town & Country, MO (US); Victor Spivak, Kiriat Bialik (IL); Evgeni Spivak, legal representative, Berlin (DE)

(73) Assignee: Vascular Imaging Corporation, Rancho Cordova, CA (US)

( * ) Notice: Subject to any disclaimer, the term of this patent is extended or adjusted under 35 U.S.C. 154(b) by 1066 days.

This patent is subject to a terminal disclaimer.

(21) Appl. No.: 12/020,736

(22) Filed: Jan. 28, 2008

(65) Prior Publication Data

US 2008/0119739 A1  May 22, 2008

Related U.S. Application Data

(63) Continuation of application No. 10/685,226, filed on Oct. 14, 2003, now Pat. No. 7,527,594, which is a (Continued)

(51) Int. Cl.
*A61B 8/14* (2006.01)
*A61B 5/00* (2006.01)

(Continued)

(52) U.S. Cl.
CPC ........ *G01H 9/004* (2013.01); *A61B 2019/5217* (2013.01); *A61B 5/0097* (2013.01); *A61B 8/12* (2013.01); *A61B 5/0095* (2013.01); *A61B 2017/22042* (2013.01)
USPC ........... 600/463; 600/407; 600/585; 600/437; 600/472

(58) Field of Classification Search
CPC ...... A61B 5/0095; A61B 5/0097; A61B 8/12; A61B 2017/22042; A61B 2019/5217; G01H 9/004
USPC ........... 385/1, 7, 37, 70, 89; 359/305; 367/11, 367/189; 398/141; 606/15; 600/407, 600/437–472, 585; 128/916

See application file for complete search history.

(56) References Cited

U.S. PATENT DOCUMENTS 4,068,191 A * 1/1978 Zemon et al. ..................... 385/1
4,076,379 A   2/1978 Chouinard (Continued)

FOREIGN PATENT DOCUMENTS

CA   2472877        7/2003
DE   2363984 A1     6/1975

(Continued)

OTHER PUBLICATIONS

"European Search Report for corresponding European Application No. EP 05 02 4287", (Dec. 16, 2005), 3 pgs.

(Continued)

*Primary Examiner* — Long V. Le
*Assistant Examiner* — Bo J Peng
(74) *Attorney, Agent, or Firm* — Schwegman Lundberg & Woessner, P.A.

(57) ABSTRACT

The present invention is a guide wire imaging device for vascular or non-vascular imaging utilizing optic acoustical methods, which device has a profile of less than 1 mm in diameter. The ultrasound imaging device of the invention comprises a single mode optical fiber with at least one Bragg grating, and a piezoelectric or piezo-ceramic jacket, which device may achieve omnidirectional (360°) imaging. The imaging guide wire of the invention can function as a guide wire for vascular interventions, can enable real time imaging during balloon inflation, and stent deployment, thus will provide clinical information that is not available when catheter-based imaging systems are used. The device of the invention may enable shortened total procedure times, including the fluoroscopy time, will also reduce radiation exposure to the patient and to the operator.

27 Claims, 5 Drawing Sheets

Related U.S. Application Data continuation of application No. 09/623,248, filed as application No. PCT/US99/04913 on Mar. 5, 1999, now Pat. No. 6,659,957.

(60) Provisional application No. 60/076,862, filed on Mar. 5, 1998.

(51) Int. Cl.
*A61B 8/12* (2006.01)
*G01H 9/00* (2006.01)
*A61B 19/00* (2006.01)
*A61B 17/22* (2006.01)

(56) References Cited

U.S. PATENT DOCUMENTS

| | | | |
|---|---|---|---|
| 4,115,753 A * | 9/1978 | Shajenko | 340/854.7 |
| 4,473,065 A | 9/1984 | Bates | |
| 4,522,193 A | 6/1985 | Bates | |
| 4,587,972 A | 5/1986 | Morantte, Jr. | |
| 4,887,605 A * | 12/1989 | Angelsen et al. | 600/439 |
| 4,900,921 A | 2/1990 | Spillman, Jr. | |
| 4,917,097 A | 4/1990 | Proudian et al. | |
| 4,946,238 A | 8/1990 | Sashin et al. | |
| 5,007,705 A | 4/1991 | Morey et al. | |
| 5,070,882 A | 12/1991 | Bui et al. | |
| 5,095,911 A | 3/1992 | Pomeranz | |
| 5,099,090 A | 3/1992 | Allan et al. | |
| 5,109,463 A | 4/1992 | Lee | |
| 5,135,295 A * | 8/1992 | Jen et al. | 385/13 |
| 5,135,486 A | 8/1992 | Eberle et al. | |
| 5,156,772 A | 10/1992 | Allan et al. | |
| 5,167,233 A | 12/1992 | Eberle et al. | |
| 5,183,048 A | 2/1993 | Eberle | |
| 5,186,177 A | 2/1993 | O'Donnell et al. | |
| 5,226,847 A | 7/1993 | Thomas, III et al. | |
| 5,240,004 A | 8/1993 | Walinsky et al. | |
| 5,254,112 A * | 10/1993 | Sinofsky et al. | 606/7 |
| 5,290,275 A | 3/1994 | Kittrell et al. | |
| 5,305,758 A | 4/1994 | Dietz et al. | |
| 5,353,262 A * | 10/1994 | Yakymyshyn et al. | 367/149 |
| 5,368,037 A | 11/1994 | Eberle et al. | |
| 5,383,467 A | 1/1995 | Auer et al. | |
| 5,400,788 A | 3/1995 | Dias et al. | |
| 5,427,107 A | 6/1995 | Milo et al. | |
| 5,439,000 A | 8/1995 | Gunderson et al. | |
| 5,453,575 A | 9/1995 | O'Donnell et al. | |
| 5,486,170 A | 1/1996 | Winston et al. | |
| 5,558,669 A | 9/1996 | Reynard | |
| 5,582,171 A | 12/1996 | Chornenky et al. | |
| 5,601,087 A | 2/1997 | Gunderson et al. | |
| 5,603,327 A | 2/1997 | Eberle et al. | |
| 5,615,675 A | 4/1997 | O'Donnell et al. | |
| 5,660,180 A | 8/1997 | Malinowski et al. | |
| 5,675,674 A | 10/1997 | Weis | |
| 5,680,489 A | 10/1997 | Kersey | |
| 5,682,897 A | 11/1997 | Pomeranz | |
| 5,684,297 A | 11/1997 | Tardy | |
| 5,704,361 A | 1/1998 | Seward et al. | |
| 5,718,226 A | 2/1998 | Riza | |
| 5,732,046 A | 3/1998 | O'Donnell et al. | |
| 5,748,564 A | 5/1998 | Pattanayak | |
| 5,779,643 A | 7/1998 | Lum et al. | |
| 5,779,644 A | 7/1998 | Eberle et al. | |
| 5,830,145 A | 11/1998 | Tenhoff | |
| 5,852,233 A | 12/1998 | Arnold et al. | |
| 5,857,974 A | 1/1999 | Eberle et al. | |
| 5,865,178 A | 2/1999 | Yock | |
| 5,872,879 A | 2/1999 | Hamm | |
| 5,876,344 A | 3/1999 | Baker et al. | |
| 5,894,531 A | 4/1999 | Alcoz | |
| 5,921,931 A | 7/1999 | O'Donnell et al. | |
| 5,938,609 A | 8/1999 | Pomeranz | |
| 5,938,615 A | 8/1999 | Eberle et al. | |
| 5,944,687 A | 8/1999 | Benett et al. | |
| 5,953,477 A | 9/1999 | Wach et al. | |
| 5,980,117 A | 11/1999 | Feuer et al. | |
| 6,039,701 A | 3/2000 | Sliwa et al. | |
| 6,049,958 A | 4/2000 | Eberle et al. | |
| 6,057,927 A | 5/2000 | Levesque et al. | |
| 6,078,831 A | 6/2000 | Belef et al. | |
| 6,080,109 A | 6/2000 | Baker et al. | |
| 6,100,969 A | 8/2000 | Perez | |
| 6,111,645 A | 8/2000 | Tearney et al. | |
| 6,123,673 A | 9/2000 | Eberle et al. | |
| 6,134,003 A | 10/2000 | Tearney et al. | |
| 6,210,339 B1 | 4/2001 | Kiepen et al. | |
| 6,222,970 B1 | 4/2001 | Wach et al. | |
| 6,228,078 B1 | 5/2001 | Eggers et al. | |
| 6,238,347 B1 | 5/2001 | Nix et al. | |
| 6,248,076 B1 | 6/2001 | White et al. | |
| 6,261,246 B1 | 7/2001 | Pantages et al. | |
| 6,282,011 B1 | 8/2001 | Tearney et al. | |
| 6,283,920 B1 | 9/2001 | Eberle et al. | |
| 6,292,610 B1 | 9/2001 | O'Rourke et al. | |
| 6,306,096 B1 | 10/2001 | Seward et al. | |
| 6,315,732 B1 | 11/2001 | Suorsa et al. | |
| 6,330,383 B1 | 12/2001 | Cai et al. | |
| 6,379,325 B1 | 4/2002 | Benett et al. | |
| 6,416,234 B1 | 7/2002 | Wach et al. | |
| 6,421,164 B2 | 7/2002 | Tearney et al. | |
| 6,494,836 B2 | 12/2002 | Ogawa | |
| 6,538,807 B2 | 3/2003 | Kakui et al. | |
| 6,575,965 B1 | 6/2003 | Fitch et al. | |
| 6,585,660 B2 | 7/2003 | Dorando et al. | |
| 6,611,633 B1 | 8/2003 | Vohra et al. | |
| 6,618,916 B1 | 9/2003 | Eberle et al. | |
| 6,659,957 B1 * | 12/2003 | Vardi et al. | 600/467 |
| 6,779,257 B2 | 8/2004 | Kiepen et al. | |
| 6,783,494 B2 | 8/2004 | Ogawa | |
| 6,907,163 B2 | 6/2005 | Lewis | |
| 6,948,859 B2 | 9/2005 | Anderson | |
| 7,082,238 B2 | 7/2006 | Nishimura | |
| 7,184,148 B2 | 2/2007 | Alphonse | |
| 7,190,464 B2 | 3/2007 | Alphonse | |
| 7,242,480 B2 | 7/2007 | Alphonse | |
| 7,242,832 B2 | 7/2007 | Carlin et al. | |
| 7,245,789 B2 | 7/2007 | Bates et al. | |
| 7,417,740 B2 | 8/2008 | Alphonse et al. | |
| 7,447,388 B2 | 11/2008 | Bates et al. | |
| 7,527,594 B2 * | 5/2009 | Vardi et al. | 600/467 |
| 7,599,588 B2 | 10/2009 | Eberle et al. | |
| 7,660,492 B2 | 2/2010 | Bates et al. | |
| 7,881,573 B2 | 2/2011 | Eberle et al. | |
| 8,059,923 B2 | 11/2011 | Bates et al. | |
| 8,218,927 B2 | 7/2012 | Chang et al. | |
| 8,391,652 B2 | 3/2013 | Bates et al. | |
| 8,560,048 B2 | 10/2013 | Eberle et al. | |
| 8,731,340 B2 | 5/2014 | Bates et al. | |
| 2001/0021843 A1 | 9/2001 | Bosselmann et al. | |
| 2002/0039463 A1 | 4/2002 | Degertekin et al. | |
| 2002/0041735 A1 | 4/2002 | Cai et al. | |
| 2003/0026546 A1 | 2/2003 | Deliwala | |
| 2003/0181802 A1 | 9/2003 | Ogawa | |
| 2003/0187369 A1 | 10/2003 | Lewis et al. | |
| 2004/0067000 A1 | 4/2004 | Bates et al. | |
| 2004/0116800 A1 | 6/2004 | Helfer et al. | |
| 2004/0182315 A1 | 9/2004 | Laflamme, Jr. et al. | |
| 2005/0131289 A1 | 6/2005 | Aharoni et al. | |
| 2005/0238292 A1 | 10/2005 | Barnes et al. | |
| 2006/0067616 A1 | 3/2006 | Kanji et al. | |
| 2007/0116408 A1 | 5/2007 | Eberle et al. | |
| 2007/0133925 A1 | 6/2007 | Bates et al. | |
| 2008/0077225 A1 | 3/2008 | Carlin et al. | |
| 2009/0059727 A1 | 3/2009 | Bates et al. | |
| 2010/0014810 A1 | 1/2010 | Eberle et al. | |
| 2010/0087732 A1 | 4/2010 | Eberle et al. | |
| 2010/0135111 A1 | 6/2010 | Bates et al. | |
| 2011/0123154 A1 | 5/2011 | Eberle et al. | |
| 2012/0108943 A1 | 5/2012 | Bates et al. | |

(56) References Cited

U.S. PATENT DOCUMENTS

| | | | |
|---|---|---|---|
| 2013/0148933 A1 | 6/2013 | Eberle et al. | |
| 2013/0178729 A1 | 7/2013 | Bates et al. | |
| 2014/0142414 A1 | 5/2014 | Eberle et al. | |

FOREIGN PATENT DOCUMENTS

| | | | |
|---|---|---|---|
| EP | 0 478 410 A1 | 4/1992 | |
| EP | 0478410 A1 | 4/1992 | |
| EP | 1059878 A1 | 12/2000 | |
| EP | 1152240 A2 | 11/2001 | |
| GB | 2 270 159 A | 3/1994 | |
| GB | 2270159 A | 3/1994 | |
| JP | 05-015536 A | 1/1993 | |
| JP | 05-220152 A | 8/1993 | |
| JP | 09-187513 A | 7/1997 | |
| JP | 10-505920 A | 6/1998 | |
| JP | 10-507036 A | 7/1998 | |
| JP | 10-510364 A | 10/1998 | |
| JP | 11-194280 A | 7/1999 | |
| JP | 11-514432 A | 12/1999 | |
| JP | 2000508939 A | 7/2000 | |
| JP | 5445736 B2 | 1/2014 | |
| WO | WO 99/58059 | 11/1999 | |
| WO | WO-9958059 A1 | 11/1999 | |
| WO | WO-0049938 A1 | 8/2000 | |
| WO | WO-01/21244 | 3/2001 | |
| WO | WO-0219898 A3 | 3/2002 | |
| WO | WO 02/054948 | 7/2002 | |
| WO | WO-02054948 A1 | 7/2002 | |
| WO | WO-02075404 A1 | 9/2002 | |
| WO | WO-03057061 | 7/2003 | |
| WO | WO-2004008070 | 1/2004 | |
| WO | WO-2004029667 | 4/2004 | |
| WO | WO-2004032746 A2 | 4/2004 | |
| WO | WO-2004077100 | 9/2004 | |
| WO | WO-2004090484 | 10/2004 | |
| WO | WO-2007062050 A2 | 5/2007 | |
| WO | WO-2007062050 A3 | 5/2007 | |

OTHER PUBLICATIONS

"International Application No. PCT/US2003/031280 International Search Report mailed Jul. 19, 2004", 8 pgs.
"International Application No. PCT/US2003/031280 Written Opinion mailed Jan. 14, 2005", 16 pgs.
"International Preliminary Examination Report (IPER)", PCT/US03/31280, (Feb. 1, 2005), 16.
"International Search Report and Written Opinion for Application No. PCT/US2006/045080", 16 Pages.
"Partial International Search Report for corresponding PCT Application No. PCT/US2006/045080", (Mar. 9, 2007), 3 pgs.
"PCT Application No. PCT/US2006/045080, International Search Report mailed May 16, 2007", 6 pgs.
"PCT Written Opinion", PCT/US03/31280, (Jan. 14, 2005), 7 pages.
"Published International Search Report for PCT/US2003/031280 (WO 2004/032746 A3)", (Apr. 22, 2004), 7 pages.
"Tissue Characterization through Ultrasonic Backscatter", http://www.brl.uiuc.edu/Projects/backscatter.htm, (viewed web site on Sep. 25, 2002), pp. 1-5.
Bates, Kenneth N., "A high acuity 3-D acoustic imaging system", *Proceedings., 1995 IEEE Ultrasonics Symposium*, 2, (Nov. 7-10, 1995), 1245-1250.
Bates, K. N., "A High Acuity 3D Acoustic Imaging System", *Proceedings., 1995 IEEE Ultrasonics Symposium*, 2, (Nov. 7-10, 1995), 1245-1250.
Bates, K. N., "A One Dimensional Phased Array Imaging System", *Ph.D. Dissertation, Applied Physics, Standford University*, (1982).
Bates, Kenneth N., et al., "Digitally Controlled Electronically Scanned and Focused Ultrasonic Imaging System", *IEEE Ultrasonics Symposium Proceedings*, 1979, (Sep. 26-28, 1979), 216-220.
Bates, K. N., et al., "PEOATS and ESOATS", *IEEE Ultrasonics Symposium Proceedings*, 1979, (Sep. 26-28, 1979), 189-194.
Bates, K. N., "Tolerance Analysis for Phased Arrays", *Acoustic Imaging*, 9, (1980), 239-262.
Blotekjaer, K., "Theoretical concepts of a novel Vernier-based fringe-counting fibre optic sensor", *IEE Proceedings, Optoelectronics*, 144(3), (Jun. 1997), 126-129.
Brady, G. P., et al., "Simultaneous measurement of strain and temperature using the first- and second-order diffraction wavelengths of Bragg gratings", *IEE Proceedings, Optoelectronics*, 144(3) (Jun. 1997), 156-161
Buma, T., et al., "A high frequency utlrasound array element using thermoelastic expansion in PDMS", *Proceedings of the 2001 IEEE Ultrasonics Symposium*, 2, (Oct. 7-10, 2001), 1143-1146.
Buma, T., et al., "A high frequency utlrasound array element using thermoelastic expansion in PDMS", *2001 IEEE Ultrasonics Symposium. Proceedings. An International Symposium*, 2(2), (Oct. 7-10, 2001), 1143-6.
Buma, T., et al., "A high-frequency, 2-D array element using thermoelastic expansion in PDMS", *IEEE Transactions on Ultrasonics, Ferroelectrics and Frequency Control*, 50(9), (Sep. 2003), 1161-1176.
Buma, T., et al., "High Frequency Ultrasonic Imaging Using Optoacoustic Arrays", *Proceedings of the Proceeding of the 2002 IEEE Ultrasonics Symposium*, 1, Invited paper,(Oct. 8-11, 2002), 571-580.
Buma, T., et al., "High Frequency Ultrasound Array Element using Thermoelastic Expansion in an Elastomeric Film", *Applied Physics Letters*, 79(4), (Jul. 23, 2001), 548-550.
Buma, T., et al., "High-frequency ultrasound imaging using opto-acoustic arrays", *Proceedings of the SPIE—The International Society for Optical Engineering*, 4687, (2002), 99-109.
Buma, T., et al., "Thermoelastic Expansion versus Piezoelectricity for High Frequency 2-D Arrays", *IEEE Transactions on Ultrasonics, Ferroelectrics and Frequency Control*, 50(8), (Aug. 2003), 1065-1068.
Buma, T., et al., "Thermoelastic Generation of Continuous Lamb Waves for Microfluidic Devices", *Proceedings of the 2003 IEEE Utlransonic Symposium*, (2003), 150-153.
Buma, T., et al., "Thermoelastic Generation of Ultrasound Using anErbium Doped Fiber Amplifier", *Proceedings of the 1999 IEEE Utlrasonics Symposium*, 2, (Oct. 17-20, 1999), 1253-1256.
Davis, M. A., et al., "Simultaneous measurement of temperature and strain using fibre Bragg gratings and Brillouin scattering", *IEE Proceedings, Optoelectronics*, 144(3), (Jun. 1997), 151-155.
Feced, R., et al., "Advances in high resolution distributed temperature sensing using the time-correlated single photon counting technique", *IEE Proceedings, Optoelectronics*, 144(3), (Jun. 1997), 183-188.
Furstenau, N., et al., "Extrinsic Fabry-Perot interferometer vibration and acoustic sensor systems for airport ground traffic monitoring", *IEE Proceedings, Optoelectronics*, 144(3), (Jun. 1997), 134-144.
Hamilton, J. D., et al., "An active optical detector for high frequency ultrasound imaging", *Proceedings of the 1997 IEEE Ultrasonics Symposium*, 1, (Oct. 5-8, 1997), 753-756.
Hamilton, J. D., et al., "High frequency optoacoustic arrays using etalon detection", *IEEE Transactions on Ultrasonics, Ferroelectrics and Frequency Control*, 47(1), (Jan. 2000), 160-169.
Hamilton, J. D., et al., "High Frequency Ultrasound Imaging Using an Active optical Detector", *IEEE Transactions on Ultrasonics, Ferroelectrics and Frequency Control UFFC-45*, (1998), 719-727.
Hamilton, J. D., et al., "High Frequency Ultrasound Imaging with Optical Arrays", *IEEE Transactions on Ultrasonics, Ferroelectrics and Frequency Control*, 45(1), (Jan. 1998), 216-235.
Hamilton, J. D., et al., "Optical Arrays for High Frequency Ultrasound Imaging", *Proceedings of the 1996 IEEE Ultrasonics Symposium*, (1996), 1419-1422.
Karl, W C., "Multi-Sensor Fusion for Atherosclerotic Plaque Characterization", Boston Univ—MDSP, 15 pages, (obtained from the internet on Sep. 25, 2002, http://www.censsis.neu/Education/StudentResearch/2001/posters/weisensell)r!.pdf.

(56) References Cited

OTHER PUBLICATIONS

Komiyama, N., et al., "Tissue Characterization of Atherosclerotic Plaques by Intravascular Ultrasound Radiofrequency Signal Analysis: An In Vitro Study of Human Coronary Arteris", *Entrez-PubMed*—(http://www.ncbi.nlm.nih.gov/entrez/query)—viewed web site on Sep. 25, 2002, pp. 1-2.

Krass, S., et al., "P3.4 Pattern Reconition Algorithms for Tissue Characterisation in Intracoronary Ultrasound Imaging: Test Data Set and Results of Computerised Texture Analysis", *2nd Medical Clinic, Univ-Mainz*, Germany—(http://www.uni-mainz.de/Cardio/incis/Data/p3_4.htm)—view web site on Sep. 25, 2002, pp. 1-3.

Lockey, R. A., et al., "Multicomponent time-division-multiplexed optical fibre laser Doppler anemometry", *IEE Proceedings, Optoelectronics*, 144(3), (Jun. 1997), 168-175.

MacPherson, W. N., et al., "Phase demodulation in optical fibre Fabry-Perot sensors with inexact phase steps", *IEE Proceedings, Optoelectronics*, 144(3), (Jun. 1997), 130-133.

McCulloch, S., et al., "Development of a fibre optic micro-optrode for intracellular pH measurements", *IEE Proceedings, Optoelectronics*, 144(3), (Jun. 1997), 162-167.

Mintz, Gary S., et al., "American College of Cardiology Clenical Expert Consensus Document on Standards for Acquistions, Measurement and Reporting of Intravascular Ultrasound Studies (IVUS)", *Journal of the American College of Cardiology*, 37(5), (Apr. 2001), 1478-1492.

O'Donnell, M., "New Imaging Technologies for Ultrasonography", *J Med Utlrason.*, 27(4), Presented at the 73rd Japan Society of Ultrasound in Medicine Meeting, Invited Paper,(2000), 356-357.

O'Donnell, M., et al., "Optoacoustics: high frequency ultrasonic array imaging", *Proceedings of 17th International Congress on Acoustics*, vol. IV, Biomedicine, Acoustics in Medicine, Invited Presentation at the 17th Intl Congress on Acoustics, Rome,(Sep. 2-7, 2001), 2-3.

Othonos, A., et al., "In Section 7.9 Bragg Gating Fiber Laser Sensors from Fiber Bragg Gratings: fundamentals and applications in telecommunications and sensing", (*1999 Artech House, Inc.*). 355-367.

Pepine, Carl J., et al., "Improving Diagnostic and Therapeutic Outcomes Through Advanced Intravascular Imaging", *Vascular Technologies, Inc.*, (1989).

Scully, P. J., "UV Laser Photo-induced Refractive Index Changes in Poly-Methyl-Meth-Acrylate and Plastic Optical Fibres for Application as Sensors and Devices", *Central Laser Facility Annual Report*, 1999/2000, (1999-2000), 145-147.

Spisar, M., et al., "Stabilized, Resonant Optoacoustic Array Detectors for Medical Imaging", *Proceedings of the World Congress on Ultrasonics*, Paris, France,(Sep. 7-10, 2003), 25-28.

Stefanadis, Christodoulos, et al., "Identification and Stabilization of Vulnerable Atherosclerotic Plaques: The Role of Coronary Thermagraphy and External Heat Delivery", *Identification and Stabilization of Vulnerable Atherosclerotic Plaques IHJ*—(viewed web site on Sep. 25, 2002), http://www.indianheartjournal.org,(2001),1-10.

Surowiec, J., et al., "A Novel Miniature Optical Fibre Probe for MHz Frequency Ultrasonics", *Proceedings, IEEE Ultrasonics Symposium*, vol. 2, San Antonio, TX),(1996), 1051-1054.

Tanaka, S., et al., "Fibre optic spectral polarimetry for sensing multiple stress-loaded locations along a length of fibre", *IEE Proceedings, Optoelectronics*, 144(3), (Jun. 1997), 176-182.

Wahle, Andreas, et al., "Accurate Visualization and Quantification of Coronary Vasculature by 3-D/4-D Fusion from Biplane Angiography and Intravascular Ultrasound", *In: Biomonitorinq and Endoscopy Technologies*; I. Gannot et al., eds, (Jul. 5-6, 2000), 144-155.

Yoshino, T., et al., "Spiral fibre microbend sensors", *IEE Proceedings, Optoelectronics*, 144(3), (Jun. 1997), 145-150.

"U.S. Appl. No. 11/285,449 Notice of Allowance mailed on May 27, 2009", 6 pgs.

"U.S. Appl. No. 11/285,499, Amendment and Response filed May 27, 2008 to Final Office Action mailed Jan. 25, 2008", 9 pgs.

"U.S. Appl. No. 11/285,499, Final Office Action mailed Jan. 25, 2008", 7 pgs.

"U.S. Appl. No. 11/285,499, Non-Final Office Action mailed on Nov. 13, 2008", 7 pgs.

"U.S. Appl. No. 11/285,499, Response filed Apr. 13, 2009 to Non Final Office Action mailed Nov. 13, 2008", 14 pgs.

"U.S. Appl. No. 11/674,568, Notice of Allowance mailed Jun. 25, 2008", 4 pgs.

"U.S. Appl. No. 12/263,978, Notice of Allowance mailed Sep. 22, 2009", 6 pgs.

"U.S. Appl. No. 12/572,511 Notice of Allowance mailed Sep. 23, 2010", 6 pgs.

"U.S. Appl. No. 12/572,511, Non-Final Office Action mailed Jun. 1, 2010", 8 pgs.

"U.S. Appl. No. 12/572,511, Response filed May 17, 2010 to Restriction Requirement mailed May 10, 2010", 7 pgs.

"U.S. Appl. No. 12/572,511, Response filed Sep. 1, 2010 to Non Final Office Action mailed Jun. 1, 2010", 9 pgs.

"U.S. Appl. No. 12/572,511, Restriction Requirement mailed May 10, 2010", 5 pgs.

"U.S. Appl. No. 12/701,228, Notice of Allowance mailed Apr. 22, 2011", 8 pgs.

"U.S. Appl. No. 11/674,568, Response filed Apr. 21, 2008 to Non Final Office Action mailed Jan. 7, 2008", 7 pgs.

"European Application Serial No. 06838195.3, Office Action mailed Jul. 27, 2009", 4 pgs.

"European Application Serial No. 06838195.3, Response filed Feb. 4, 2010 to Office Action mailed Jul. 27, 2009", 8 pgs.

"Japanese Application Serial No. 2000-547913, Argument and Amendment filed May 22, 2009 to Office Action mailed Feb. 24, 2009", (w/ English Translation of Amended Claims), 9 pgs.

"Japanese Application Serial No. 2000-547913, Argument and Amendment filed Dec. 18, 2009 to Office Action mailed on Jun. 23, 2009", (w/ English Translation of Amended Claims), 13 pgs.

"Japanese Application Serial No. 2000-547913, Office Action mailed Feb. 24, 2009", (w/ English Translation), 7 pgs.

"Japanese Application Serial No. 2000-547913, Office Action mailed on Jun. 23, 2009", (w/ English Translation), 8 pgs.

Takahashi, N., et al., "Underwater Acoustic Sensor with Fiber Bragg Grating", *Optical Review*, 4(6), (1997), 691-694.

"U.S. Appl. No. 12/701,228, Notice of Allowance mailed Jun. 27, 2011", 5 pgs.

"U.S. Appl. No. 13/017,354, Non Final Office Action mailed Jan. 9, 2012", 8 pgs.

"U.S. Appl. No. 13/017,354, Non Final Office Action mailed Jun. 24, 2011", 8 pgs.

"U.S. Appl. No. 13/017,354, Response filed Sep. 26, 2011 to Non-Final Office Action mailed Jun. 24, 2011", 16 pgs.

"European Application Serial No. 05024287.4, Office Action mailed Feb. 9, 2012", 4 pgs.

"U.S. Appl. No. 09/623,248, Examiner Interview Summary filed Nov. 6, 2003.", 1 pg.

"U.S. Appl. No. 10/266,082, Response filed Jul. 28, 2004 to Restriction Requirement Jun. 29, 2004", 2 pgs.

"U.S. Appl. No. 10/266,082, Restriction Requirement mailed Jun. 29, 2004", 5 pgs.

"U.S. Appl. No. 10/685,226, Preliminary Amendment filed Oct. 14, 2003", 1 pg.

"U.S. Appl. No. 10/685,226, Response filed Oct. 23, 2006 to Non Final Office Action mailed Jul. 24, 2006", 9 pgs.

"U.S. Appl. No. 11/674,568, Response filed Oct. 16, 2007 to Restriction Requirement mailed Sep. 17, 2007", 7 pgs.

"U.S. Appl. No. 12/571,724, Final Office Action mailed Jan. 4, 2013", 13 pgs.

"U.S. Appl. No. 12/571,724, Non Final Office Action mailed Apr. 18, 2012", 11 pgs.

"U.S. Appl. No. 12/571,724, Response filed Oct. 16, 2012 to Non Final Office Action mailed Apr. 18, 2012", 12 pgs.

"U.S. Appl. No. 13/285,551, Non Final Office Action mailed Apr. 12, 2012", 5 pgs.

"U.S. Appl. No. 13/285,551, Notice of Allowance mailed Nov. 5, 2012", 7 pgs.

"U.S. Appl. No. 13/285,551, Response filed Oct. 12, 2012 to Non Final Office Action mailed Apr. 12, 2012", 8 pgs.

(56) References Cited

OTHER PUBLICATIONS

"European Application Serial No. 05024287.4, Office Action mailed Sep. 25, 2012", 1 pg.

"European Application Serial No. 05024287.4, Response filed Nov. 23, 2012 to Office Action mailed Feb. 9, 2012", 9 pgs.

"European Application Serial No. 05024287.4, Response filed Nov. 23, 2012 to Office Action mailed Sep. 25, 2012", 9 pgs.

"European Application Serial No. 05024287.4, Response filed Jun. 6, 2007 to Office Action mailed Sep. 22, 2006", 8 pgs.

"European Application Serial No. 05024287.4, Search Report mailed Jan. 3, 2006", 7 pp.

"European Application Serial No. 99950325.3, European Search Report Mailed Mar. 8, 2004", 3 pp.

"European Application Serial No. 99950325.3, Examination Report Mailed Jul. 28, 2004", 3 pp.

"European Application Serial No. 99950325.3, Response filed Feb. 7, 2005 to European Search Report Mailed Mar. 8, 2004", 10 pp.

Moreira, P J, et al., "Dynamic Range Enhancement in Fiber Bragg Grating Sensors using a Multimode Laser Diode", IEEE Photonics Technology Letters, vol. 11, No. 6, (Jun. 1999), 3 pgs.

"U.S. Appl. No. 13/685,048, Notice of Allowance mailed Jun. 9, 2014", 9 pgs.

"U.S. Appl. No. 14/053,421, Non Final Office Action mailed Jun. 20, 2014", 13 pgs.

"U.S. Appl. No. 14/280,327, Preliminary Amendment field Jun. 6, 2014", 6 pgs.

"European Application Serial No. 05024287.4, Examination Notification Art. 94(3) mailed Apr. 25, 2014", 4 pgs.

"International Application Serial No. PCT/US03/31280, Demand and Response filed May 6, 2004 to Partial Search Report mailed Dec. 2, 2004", 13 pgs.

"International Application Serial No. PCT/US03/31280, Invitation to Pay Additional Fees and Partial Search Report mailed Feb. 12, 2004", 10 pgs.

"International Application Serial No. PCT/US2006/045080, Invitation to Pay Additional Fees and Partial International Search Report mailed Mar. 9, 2007", 4 pgs.

"U.S. Appl. No. 11/285,499, Examiner Interview Summary mailed May 18, 2009", 4 pgs.

"U.S. Appl. No. 12/571,724, Examiner Interview Summary mailed May 22, 2013", 3 pgs.

"U.S. Appl. No. 12/571,724, Notice of Allowance mailed Jun. 11, 2013", 6 pgs.

"U.S. Appl. No. 12/571,724, Response filed Jun. 4, 2013 to Final Office Action mailed Jan. 4, 2013", 13 pgs.

"U.S. Appl. No. 13/685,048, Non Final Office Action mailed Aug. 29, 2013", 10 pgs.

"U.S. Appl. No. 13/685,048, Notice of Allowance mailed Feb. 20, 2014", 9 pgs.

"U.S. Appl. No. 13/685,048, Notice of Allowance mailed Nov. 22, 2013", 10 pgs.

"U.S. Appl. No. 13/685,048, Response filed Dec. 6, 2013 to Non Final Office Action mailed Aug. 29, 2013", 11 pgs.

"U.S. Appl. No. 13/779,985, Non Final Office Action mailed Apr. 25, 2013", 7 pgs.

"U.S. Appl. No. 13/779,985, Notice of Allowance mailed Jan. 9, 2014", 16 pgs.

"U.S. Appl. No. 13/779,985, Response filed Sep. 25, 2013 to Non Final Office Action mailed Apr. 25, 2013", 12 pgs.

"Canadian Application Serial No. 2,630,662, Office Action mailed Sep. 6, 2013", 3 pgs.

"Canadian Application Serial No. 2,630,662, Response filed Mar. 6, 2014 to Office Action mailed Sep. 6, 2013", 15 pgs.

"European Application Serial No. 05024287.4, Office Action mailed Sep. 22, 2006", 1 pg.

"International Application Serial No. PCT/US2006/045080, International Preliminary Report on Patentability mailed Jun. 5, 2008", 10 pgs.

"International Application Serial No. PCT/US99/04913, International Search Report mailed May 28, 1999", 1 pg.

"Japanese Application Serial No. 2008-541424, Amendment filed Nov. 16, 2009", w/English claims.

"Japanese Application Serial No. 2008-541424, Office Action mailed Sep. 3, 2013", w/English translation, 6 pgs.

"Japanese Application Serial No. 2008-541424, Response filed Oct. 29, 2013 to Office Action mailed Sep. 13, 2013", w/English claims, 9 pgs.

\* cited by examiner

OPITCAL-ACOUSTIC IMAGING DEVICE

I. RELATED APPLICATIONS

This application is a Continuation of U.S. application Ser. No. 10/685,226, filed on Oct. 14, 2003, now U.S. Pat. No. 7,527,594 which is a Continuation of U.S. application Ser. No. 09/623,248, filed on Jun. 11, 2002, now issued as U.S. Pat. No. 6,659,957, which is a National Stage filing under 35 U.S.C. 371 of PCT/US99/04913, filed on Mar. 5, 1999, published in English as WO 99/5059 on Nov. 18, 1999, which claims priority to U.S. Provisional Application No. 60/076, 862, filed on Mar. 5, 1998, which applications and publications are incorporated herein by reference.

II. FIELD OF THE INVENTION

The present invention relates to an omnidirectional imaging device for vascular or nonvascular imaging that may be used as an intravascular guidewire.

III. BACKGROUND OF THE INVENTION

Intra-vascular and non-vascular imaging are very important techniques that provide information that is not available by angiographic imaging methods such as information about the composition of the subject vessel wall, plaque analysis, and disease processes. It is also very important as an aid to vascular interventions, especially stent deployment.

Prior art intra-vascular ultrasound (IVUS) devices are described as generally adapted to be used via catheter, and are primarily either mechanical or solid state. In the mechanical IVUS catheter, image scanning is accomplished by a rotating drive shaft causing mechanical rotation of a miniature acoustical transmitter. The drive shaft and most of the transmitter are located within the body of a flexible catheter. The design of these devices generally creates difficulties in tracking with a limited image area, and vibration of the catheter during rotation poses a risk to the patient of arterial spasm.

The solid state IVUS catheter does not have a rotating driveshaft, but rather produces images by scanning with electrical impulses that are generated from a large number of piezoelectric elements located within the IVUS. Each piezoelectric element is controlled by a driver such as a computer. Conventional solid state IVUS devices generally have a lumen adapted to receive a guidewire, and a coaxial cable design which enhances the trackability and pushability of the device as compared to the mechanical model.

One deficiency in conventional mechanical and solid state IVUS catheters is the external diameter, generally approximately 1.2 mm. Mechanical limitations on component sizes and noise effects have thus far limited commercially feasible manufacture of a smaller diameter device. In addition, both these devices must be used with traditional intraluminal catherization methods, that is, with the catheter situated over a guidewire.

Some prior art ultrasonic catheter patents describe a thin films of a flexible piezoelectric plastic material, such as poled polyvinyldiene fluoride (PVDF), which can be spot polarized in active regions to serve as piezoelectric transducers. In these devices, the PVDF film is used both as a transmitter and as a receiver. However, it is difficult to adapt this technology to small (less than 1.2 mm diameter) imaging catheters with multiple elements, for several reasons. One such reason is the very low electrical capacitor of each of the receiver elements having a small surface area as compared to the capacitor of the long electrode conductors (more then 1 m long). This relationship of elements in the device generally results in a low signal/noise relation. While the signal to noise ration may be increased by the use of preamplifiers near the receivers, physically accommodating the preamplifiers inside of a space with an outer diameter of less than 1.2 mm is very difficult. Another reason is the large signal cross talk experienced due to the long, closely clustered conductors within the device.

Other relevant prior art technology that couples ultrasonic waves with an optical fiber in an intravascular device includes a transducer which is precisely located on thin slab of piezoelectric material. The transducer generates ultrasonic acoustic surface waves that propagate on the surface or within the bulk of the slab. These devices are limited, however, in that they generate doppler signals and not images, and their probing range is limited to the area just in front of the catheter pass. Also, the piezoelectric chip is not small enough to be used in a device with a profile diameter of less than 1 mm, and more importantly, less than 0.5 mm.

In most commercially available piezoceramic and PVDF IVUS devices, one significant problem is the difficulty in constructing ultrasound imaging catheters with a diameter of less then approx. 1 mm, and where the signal to noise ratio will be high enough for the device to be easily used. Such devices are also difficult to manufacture from a mechanical perspective, using conventional components.

Accordingly, it would be useful to have an intra-vascular ultrasound imaging device with a profile of less that approximately 1 mm in diameter and most preferably less than 0.5 mm in diameter, with a signal/noise ratio that is higher than those generated by conventional IVUS devices such as those described above. It would also be useful to have an imaging device for non-vascular applications which demand a device profile of less than 1 mm.

IV. SUMMARY OF THE INVENTION

The present invention is a guidewire imaging device for vascular or non-vascular imaging utilizing optico-acoustical methods, which device has a profile of less than 1 mm in diameter, and most preferably less than 0.5 mm in diameter. The imaging device of the invention comprises a single-mode optical fiber with at least one Bragg grating and a piezoelectric or piezoceramic jacket, which device may achieve omni-directional (360°) imaging. The imaging guidewire of the invention can function as the guidewire for vascular interventions, and can enables real time imaging during balloon inflation and stent deployment, thus will provide clinical information that is not available when catheter-based imaging systems are used. The device of the invention may enable shortened total procedure times, including the fluoroscopy time, and will also reduce radiation exposure to the patient and the operator.

Thus, it is an object of the invention to provide an optico-acoustic device for vascular or non-vascular imaging with a profile of less than 1 mm, and most preferably less than 0.5 mm.

Another object of the invention is to provide a guidewire imaging device for producing real time images during vascular intervention procedures prior to catheter insertion and throughout the procedure.

A further object of the invention is to provide a device which is capable of omnidirectional 360 degree imaging.

Still another object of the invention is to provide an intravascular imaging technique with an improved signal to noise ratio over prior art intravascular imaging devices.

V. DESCRIPTION OF THE FIGURES

VI. DESCRIPTION OF THE PREFERRED EMBODIMENTS

Figure 1:
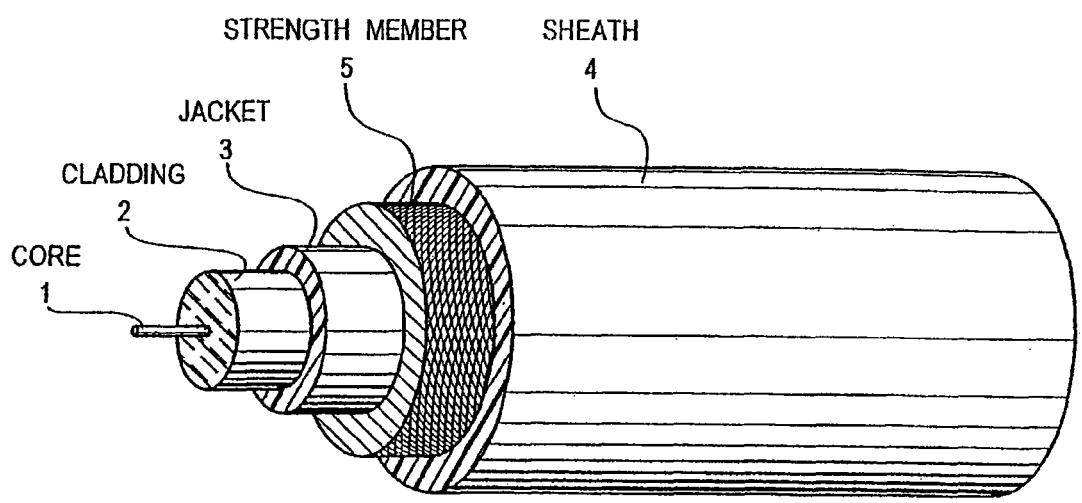
FIG. 1 is a schematic diagram of a conventional optical fiber.
Figure 2:
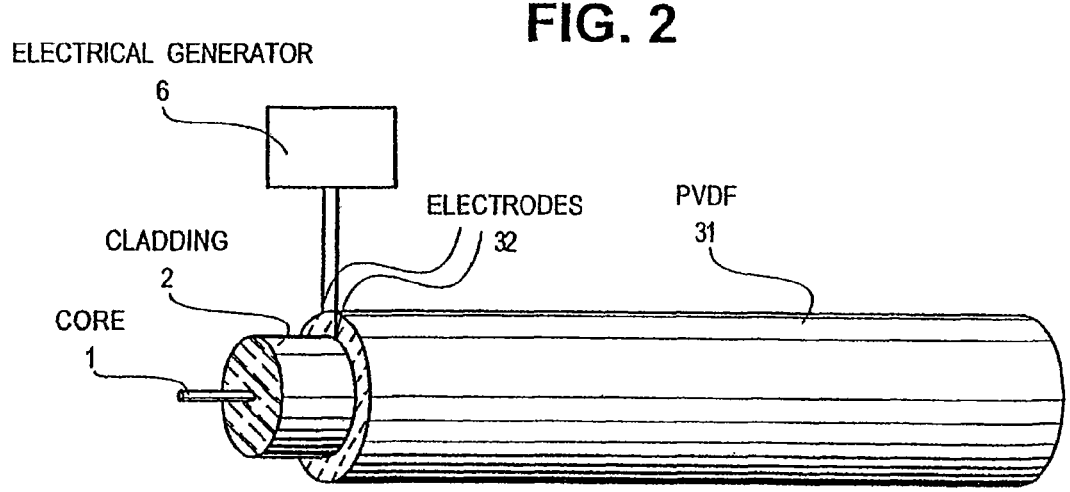
FIG. 2 is schematic diagram of a PVDF jacketed optical fiber.

The device of the invention utilizes a single optical fiber, for example but not limited to a glass fiber at least partly composed of silicon dioxide. The basic structure of a generic optical fiber is illustrated in FIG. 2, which fiber generally consists of layered glass cylinders. There is a central cylinder called the core 1. Surrounding this is a cylindrical shell of glass, possibly multilayered, called the cladding 2. This cylinder is surrounded by some form of protective jacket 3, usually of plastic (such as acrylate). For protection from the environment and more mechanical strength than jackets alone provide, fibers are commonly incorporated into cables. Typical cables have a polyethylene sheath 4 that encases the fibers within a strength member 5 such as steel or Kevlar strands.

Optical fibers can be broadly classified according to their refractive index profile and dimensions. The invention described below uses single-mode fibers.

FIG. 2 shows an optical fiber coated by a piezoelectric jacket, to which an alternating voltage electrical generator 6 is attached to electrodes 32 situated on either side of the jacket the generator 6 sends electrical impulses to the electrodes 32, which impulses cause mechanical oscillations in the jacket 31.

In recent years Fiber Bragg Grating (FBG) sensors have generated great interest because of their potential use in a wide range of applications such as telecommunications. FBGs form an integral part of the optical fiber structure and can be written intracore during manufacture or after manufacture.

Figure 3:
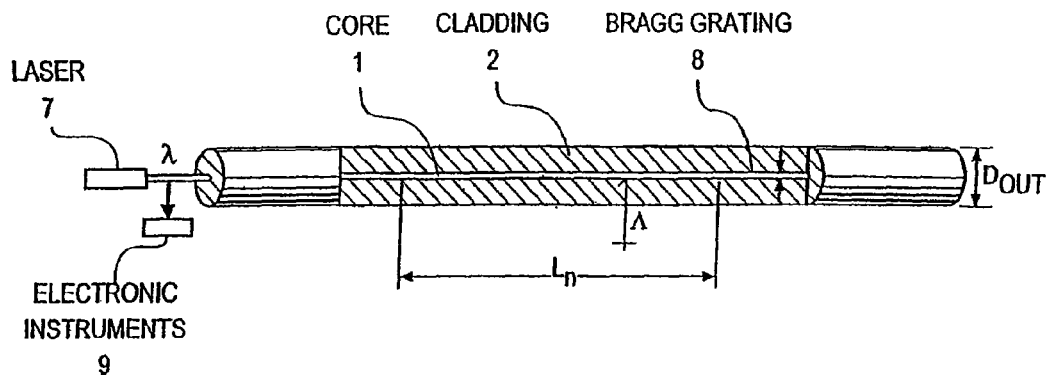
FIG. 3 is a schematic diagram of a Fiber Bragg Grating based sensor.

As illustrated in FIG. 3, when illuminated by a broadband light laser 7, a uniform pitch Fiber Bragg Grating ("FBG") element 8 will reflect back a narrowband component centered about the Bragg wavelength $\lambda$ given by $\lambda=2n\Lambda$, where n is the index of the core of the fiber and $\Lambda$ represents the grating period. Using a tunable laser 7 and different grating periods (each period is approximately 0.5µ) situated in different positions on the fiber, it is possible to make independent measurement in each of the grating positions.

Example 1

Figure 4:
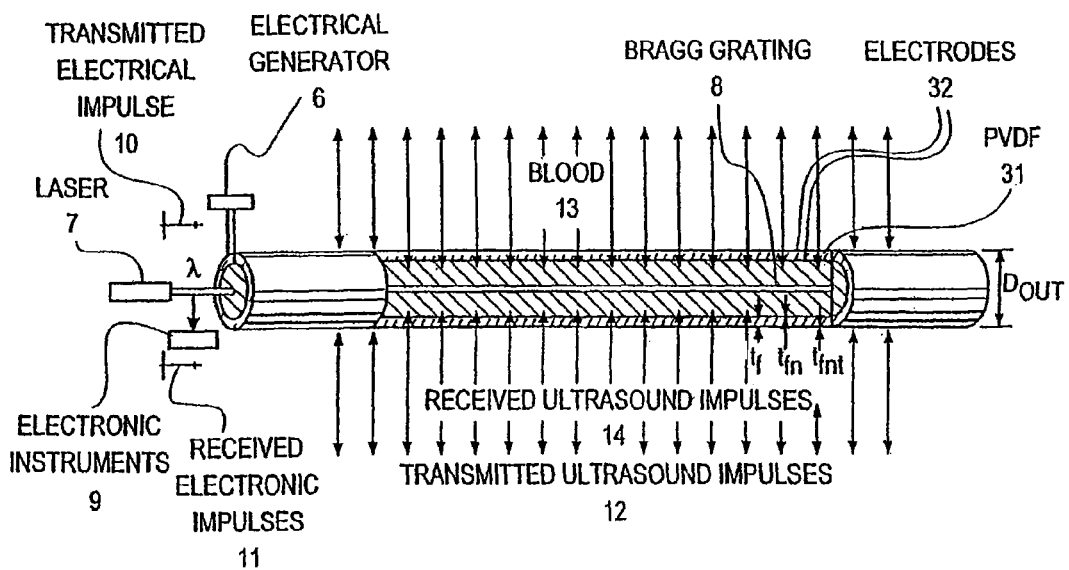
FIG. 4 is a schematic depiction of a PVDF and FBG based ultrasound pulser-receiver of the invention.

One preferred embodiment of the invention is illustrated in FIG. 4. This embodiment includes a single-mode optical fiber with a Bragg grating 8 and a piezoelectric or piezoceramic jacket 31. The jacket may be any suitable piezoelectric or piezoceramic material, and one preferable material is poled PVDF. It is contemplated that other jacket materials will work with the invention, so long as the material has suitable flexibility and piezoelectric characteristics.

In the preferred embodiment of the device of the invention as illustrated in FIG. 4, an electrical generator 6 transmits ultrasound impulses 10 to both the Bragg grating 8 and to the outer medium 13 in which the device is located, for example, the blood. Primary and reflected impulses 11 are received by the Bragg grating 8 and recorded by electronic instruments 9 using conventional methods, such as by a photodetector and an oscilloscope. From the recorded signals, a corresponding image is generated by conventional methods. Hence, the invention utilizes omnidirectional sonar (pulser-receiver) at each of the imaging locations. If mechanical deformations appear inside the optical fiber, they cause modulation of light reflected backward, which is received by the electronic instruments 9.

It is contemplated that in the various devices constructed according to the invention, the thickness of the jacket as well as the diameter of the optical fiber may vary significantly, and the only requirement is that the entire device be less than 1 mm and most preferably less than 300µ, and that the signals generated by the device are suitable to generate an image.

The ultrasound transmitter device of the invention comprises a single fiber covered by a piezoelectric active (poled) PVDF jacket has a total outside diameter of preferably less than 1 mm, and most preferably less than 300µ. It is also contemplated that devices may be made in accordance with the principles of the invention with profiles of approximately or less than 200µ. Devices with other frequency transmitters may also be constructed in accordance with the principles of the invention, as applications dictate. The device of the invention includes any needed frequency of transmitter.

Example 2

It may also be possible to expand the frequency band of the signal by using a damped silica fiber. In this variation of the preferred embodiment of the invention, frequency band expansion causes shortening of the signal in time, which improves the resolution of the received signal. For instance, using a damped fiber in a device of the invention, we have obtained maximum widths of the frequency band of the signal of approximately 110, although another variations will be achieved depending upon experimental conditions. If damped fibers are utilized, transmitters transmitting at less than 40 MHz may be used.

Example 3

Figure 5:
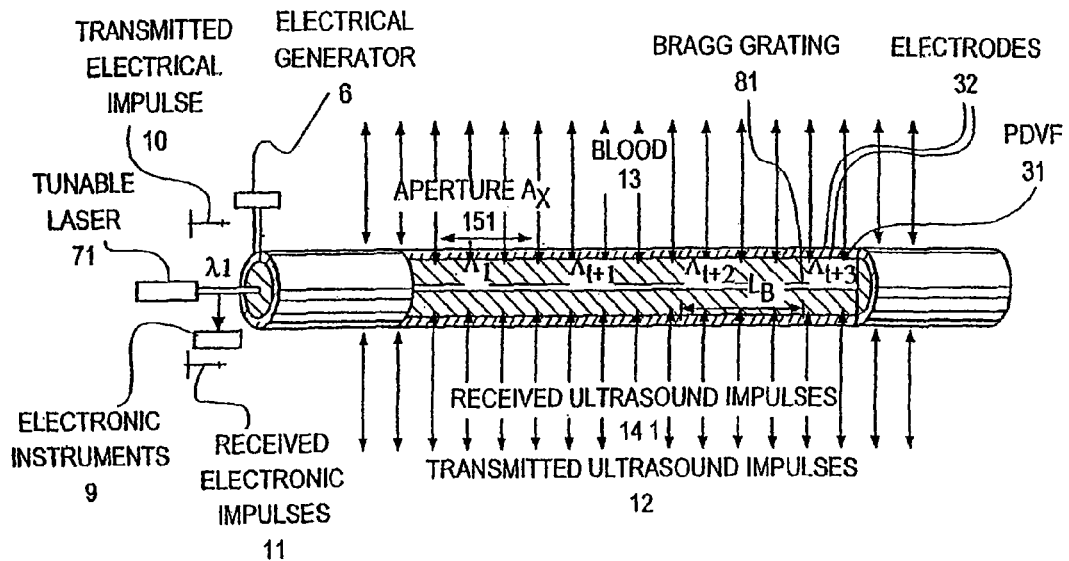
FIG. 5 is a schematic diagram of a PVDF and FBG based ultrasound pulser-receiver having a plurality of Bragg gratings.

As shown in FIG. 5, one other preferred embodiment of an imaging device in accordance with the invention comprises a plurality of Bragg gratings 81 with different periods, each period being approximately 0.5µ. By using multiple Bragg gratings, a set of distributed sonars are obtained. By utilizing a tunable laser 71 as previously described, we obtain scanning over an omnidirectional array. A Bragg grating length LB of some hundreds of optical wavelengths are sufficient to reflect considerable part of the optical beam. The ultrasound impulses 141 are received only by the Bragg gratings 81, with the period of $\Lambda_1$ which is equal to the aperture $A_x$.

Example 4

Figure 6:
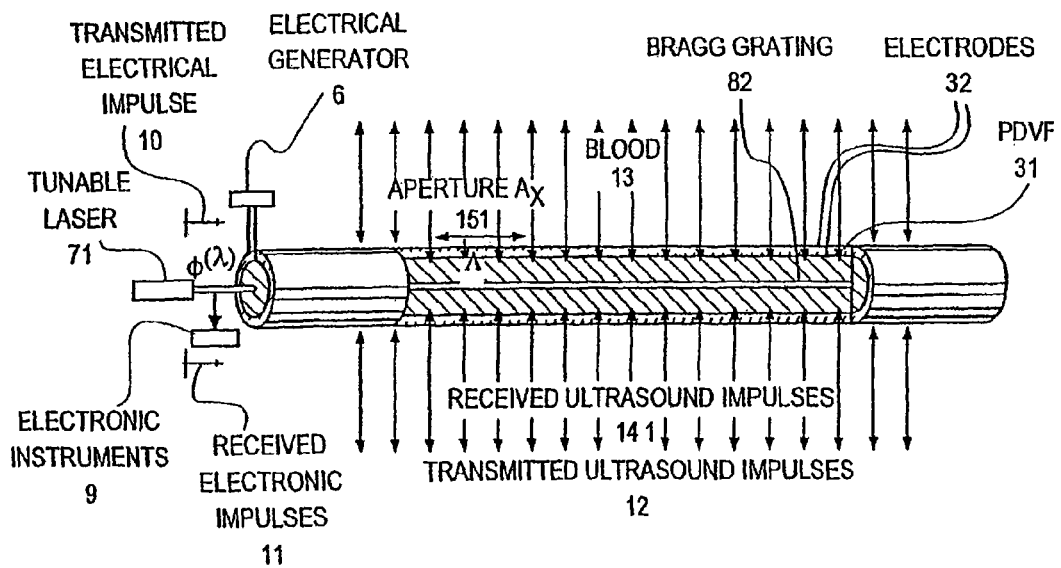
FIG. 6 is a schematic diagram of a PVDF and FBG based ultrasound pulser-receiver having a plurality of variable Bragg gratings.

In yet another preferred embodiment of a device of the invention as illustrated in FIG. 6, instead of a plurality of Bragg gratings, the device may incorporate a single variable grating, with a variable period. When a tunable laser is adjusted to the wavelength $\lambda_1$ the receiving element is the Bragg grating. When the laser wavelength is adjusted to other wavelengths $\lambda_{2-6 \ldots}$, the corresponding positioning of the Bragg grating along the axis of the fiber is also adjusted.

We have determined that for a device with a 40 MHz frequency transmitter and aperture $A_x$=151-200μ, the reception obtained by the invention provides acceptable imaging.

Example 5

Figure 7:
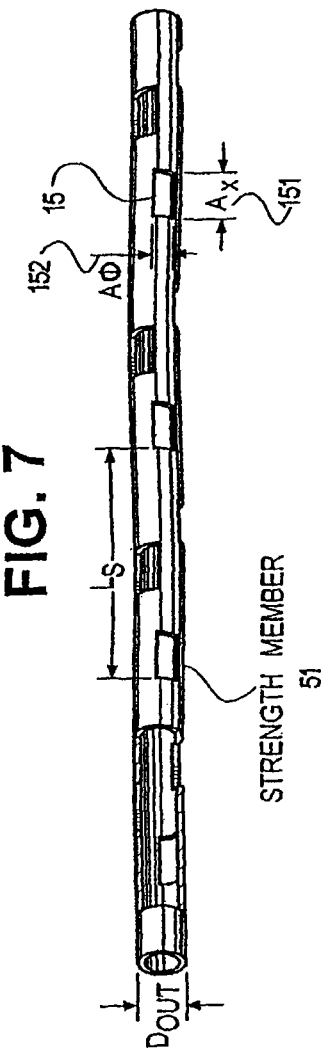
FIG. 7 is a schematic depiction of the optical fiber of the invention with a strength member.

In yet another preferred embodiment of the device of the invention as illustrated in FIG. 7, a strength member may be optionally added. This strength member is very thin, and even with the strength member, it is contemplated that the device of the invention is still less than 1 mm in diameter.

Figure 9:
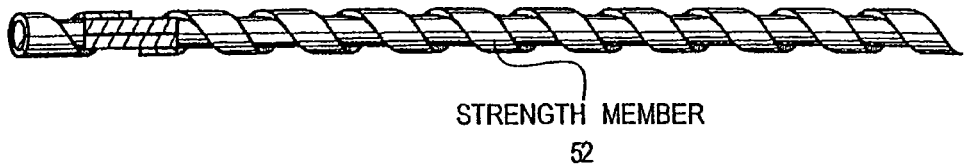
FIG. 9 is a schematic depiction of a catheter of the invention provided with a spiral strength member.

To preserve the omnidirectional scanning ability of the invention, the optical fiber is placed into the strength member 51 comprising a plurality of rectangular apertures 15. These apertures 15 have a length dimension 151 along axis x=$A_x$, and a circumferential dimension length 152=$A_{\phi\delta}$152. In a preferred embodiment the apertures are rectangular, although other shapes may be utilized. The apertures 15 may be distributed throughout the imaging portion of the device, and may be distributed in a pattern, for example a spiral as illustrated in FIG. 9.

Example 6

Figure 8:
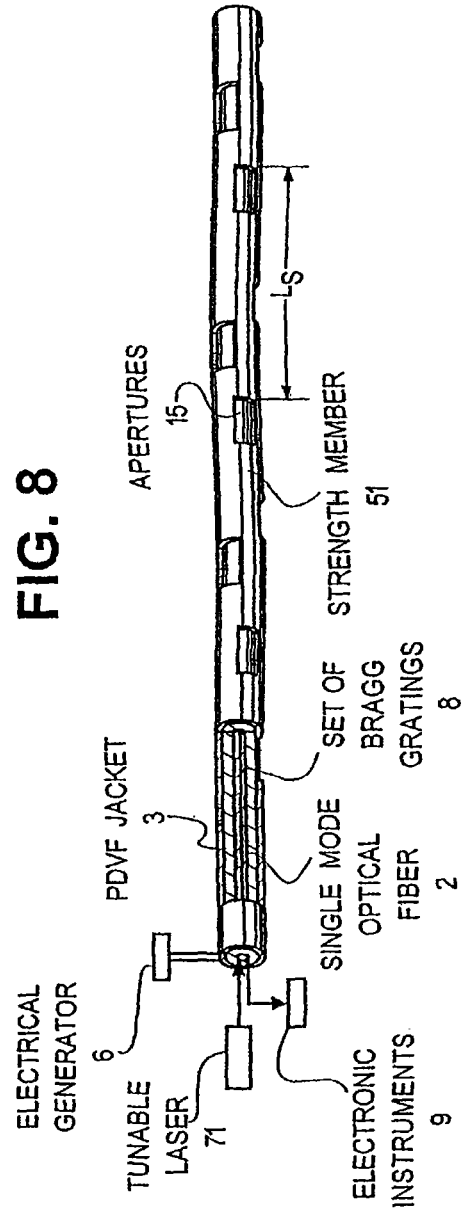
FIG. 8 is a schematic depiction of an ultrasound imaging catheter of the invention.

Example 6, as illustrated in FIG. 8, is a catheter version of the device of the invention, which produces ultrasound scanning both along the axis and along the circumference. It is comprised of a single mode optical fiber 2 with a plurality of Bragg gratings 8. The optical fiber is provided with a jacket 3, and a strength member 51, which has set of apertures 15. The strength member may be made of any hard, flexible and durable biocompatible material such as metal. Apertures are placed uniformly on the surface of strength member, both along the length and angle. The outside diameter of this device is less than 1 mm, and most preferably less than 0.5 mm. It is contemplated that the device may further have a most preferred outer diameter of less than 400μ. The apertures may be constructed using conventional photochemistry technology.

As illustrated in FIG. 8, the device is shown with an array of apertures $A_x$=$A_{\phi\delta}$=200μ, period $L_S$=1000μ. By applying electrical impulses to the electrodes of PVDF jacket 3 from electrical generator 6 we generate acoustical impulses in the all apertures simultaneously. The ultrasound impulses will expand in a direction perpendicular to the optical fiber surface, and reflect back from the nonhomogeneous medium (tissue). By tuning the laser 71, it is possible to realize scanning of the received ultrasound signals. Electronic instruments 9 receive, process and displaying the resulting images. One can estimate the scanning period $L_S$ of scanning as 0.5 to 1.0 mm lengthwise and number of directions around the fiber as 5 to 10.

Example 7

The design of the invention may also comprise more than one optical fiber. If there are a plurality of fibers within the strength member, it is possible to decrease the period and increase the number of directions of the scanning.

Example 8

FIG. 9 shows a variation of the strength member 52, comprising a spiral strength member. Use of this member is believed to produce smoother scanning, and a simpler manufacture than a strength member with apertures.

Example 9

Figure 10:
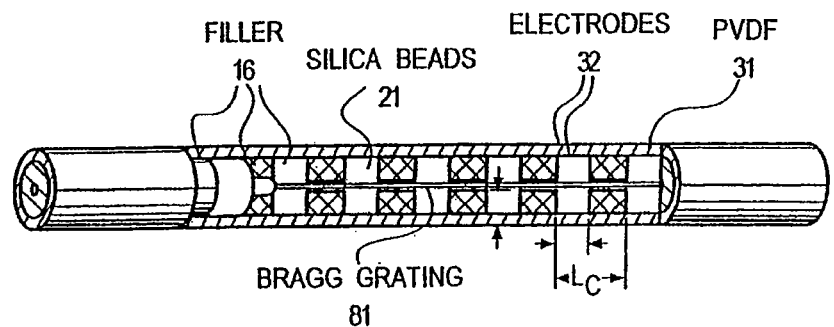
FIG. 10 is a schematic depiction of a fiber with bead-shaped cladding.

As illustrated in FIG. 10, another variation of the device of the invention is a variable diameter cladding, preferably of silica, with a period L along the fiber. This variation is achieved by the use of beads 21, which causes an increased sensitivity to acoustical waves. Maximum efficiency is achieved if the period $L_c$ is equal to one of the following resonance lengths: it is approximately equal to acoustical wavelength in water $L_{c1}$ Å $(1500/40 \cdot 10^6)$=$37.5 \cdot 10^{-6}$ m (for 40 MHz); or it is equal to the quasi-Lamb wavelength in the silica fiber $L_{c2}$.

In this embodiment, the Bragg grating interacts with optical waves and with the acoustical grating formed by the beads.

Example 10

As illustrated in FIG. 10, an additional increase in sensitivity f the device may optionally be received if a filler 16 is used to fill the gaps between the beads. This filler is produced from material with comparatively low acoustical impedance, such as a solid polymer, gel, fluid or other suitable material. For the purpose of yet additional increasing in sensitivity, gap filling filler is selected from the materials which sound velocity $c_f$ lower than sound velocity in water (blood), that is $c_f$<1500 m/sec. One example of such materials is silicon rubber having the sound velocity $c_f$~1000 m/sec. In consequence of the sound velocity difference the energy focusing is achieving. Thus, the filling material functions as a signal collecting lens.

Example 11

Figure 11:
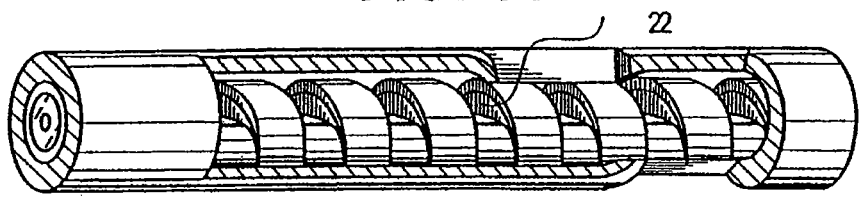
FIG. 11 is a schematic depiction of a fiber of the invention with bead cladding and with a spiral strength member.

Yet another variation of the device of the invention includes a spiral jacket 22, as shown in FIG. 11.

Example 12

Figure 12:
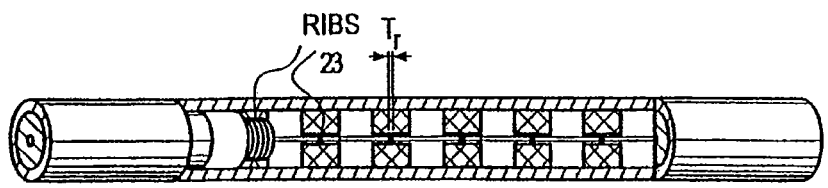
FIG. 12 is a device of the invention with bead cladding and with ribs.

Another embodiment (illustrated in FIG. 12) includes adding ribs 23 to the jacket. In one example of a device with ribs, to achieve 40 MHz resonance, silica ribs should nave approximately dimensions: height $H_r$=10 microns and thickness $T_r$=4.5 microns. The oscillations of ribs 23 induce the additional deformations at the fiber axes, hence causing the increasing in sensitivity. It is possible to fabricate ribs by conventionally known micromachining technology.

In a deviation of the ribbed embodiment, the ribs may have varying thicknesses, which are believed to lead to acoustical damping, and hence an increase in bandwith and resolution. If each of the ribs 23 will have different height $H_r$ and width $T_r$, then they will resonate at different frequencies.

Example 13

Figure 13:
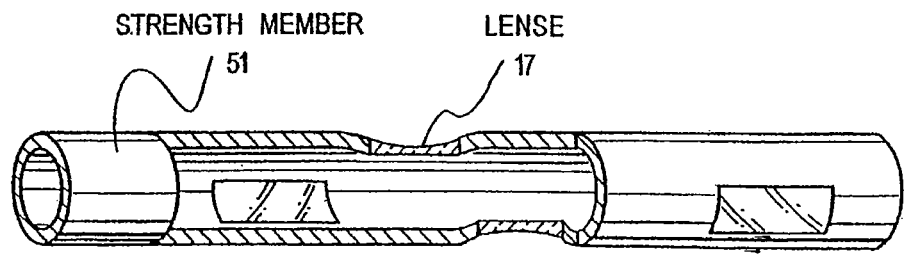
FIG. 13 is a catheter of the invention adapted with lens apertures.

For the purpose of yet additional increases in sensitivity, the apertures of the strength member may filled with a material with a velocity $c_L>1500$ m/sec, and an outside surface curvature which forms a focused lens, as illustrated in FIG. 13.

It is thus seen from the above description of the preferred embodiments that the objects of the invention are attained. Variations on this embodiment will be apparent to those skilled in the art without departing from the scope of the invention. All matter contained in the above description and the accompanying drawings is intended to be illustrative of the invention, and not limiting in the scope of the invention.

What is claimed is:

1. A device comprising:
    an elongate member including proximal and distal ends, and defining a longitudinal direction therebetween, the elongate member comprising a plurality of optical fibers extending in the longitudinal direction, wherein a distal portion of the elongate member is configured to be introduced into a human or animal body for internally imaging a portion of the body;
    a strength member disposed about the elongate member, the strength member defining a plurality of apertures;
    an acoustic transmitter on the distal portion of the elongate member that is configured to be introduced into a human or animal body for internally imaging a portion of the body; and
    an acoustic-to-optical transducer at each of a plurality of separately addressable discrete locations, the discrete locations including locations on different ones of the optical fibers and respectively corresponding to the plurality of apertures, the locations distributed around a circumference of the distal portion of the elongate member that is configured to be introduced into a human or animal body for internally imaging a portion of the body, and wherein the plurality of separately addressable discrete locations distributed around the circumference are configured to be scanned for performing the imaging in a number of different directions respectively directed outward through the plurality of apertures from the corresponding discrete locations distributed around the circumference.

2. The device of claim 1, wherein the separately addressable discrete locations include locations that are spaced apart from each other in the longitudinal direction.

3. The device of claim 1, wherein the elongate member includes a sufficiently small diameter and sufficient rigidity to permit use for introducing a separate ancillary device into the body.

4. The device of claim 1, in which the acoustic-to-optical transducer includes a Bragg grating sensor formed in a core of the optical fiber.

5. The device of claim 4, in which the Bragg grating sensor includes a variable period.

6. The device of claim 5, further including a tunable laser, optically coupled to the Bragg grating sensor including the variable period, the laser operable to adjust an effective location of the Bragg grating sensor by adjusting a wavelength of light to select a desired portion of the Bragg grating sensor that provides a corresponding desired period.

7. The device of claim 1, in which the elongate member is biocompatible and has a diameter of less than about 1 millimeter.

8. The device of claim 1, in which the optical fibers comprise at least one optical fiber including a core and a cladding about at least a portion of the core, and in which a diameter of the cladding varies longitudinally along the elongate member.

9. The device of claim 1, in which the elongate member includes an acoustic signal collecting lens.

10. A method comprising:
    delivering acoustic energy to internal locations within a body using an elongate imaging device that includes proximal and distal ends defining a longitudinal direction therebetween, the elongate member including a plurality of optical fibers that include an acoustic-to-optical transducer, wherein a circumference of the elongate member includes an acoustic-to-optical transducer at each of a plurality of separately addressable discrete locations on different ones of the optical fibers, the locations distributed around the circumference and configured to be scanned for performing imaging in a number of different directions respectively directed outward from the corresponding discrete locations distributed around the circumference and through a strength member disposed about the elongate imaging device and defining a plurality of apertures;
    receiving at the circumferentially distributed acoustic-to-optical transducers, within the body, acoustic energy reflected from the body;
    transducing, within the body, the received acoustic energy into an optical signal providing circumferentially distributed imaging information; and
    communicating the optical signal to a location outside of the body.

11. The method of claim 10, comprising adjusting a wavelength of light in the optical fiber to selectably address particular discrete locations along the elongate member.

12. The method of claim 10, comprising:
    introducing a catheter over the elongate imaging device; and
    guiding the catheter to a desired location using the elongate imaging device.

13. The method of claim 10, comprising:
    introducing a stent over the elongate imaging device; and
    positioning the stent at a desired location using the elongate imaging device.

14. The method of claim 10, in which the transducing includes using a Bragg grating.

15. An imaging device for being introduced into a human or animal body for imaging an internal portion of the body, the device comprising:
    an elongate member including proximal and distal ends, and defining a longitudinal direction therebetween, the elongate member comprising a plurality of optical fibers;
    a strength member disposed about the elongate member, the strength member defining a plurality of apertures; and
    means for performing circumferentially distributed acoustic-to-optical transducing at discrete locations on different ones of the optical fibers, the locations distributed around a circumference of the elongate member on different ones of the optical fibers and respectively corresponding to the plurality of apertures, wherein the means for performing is located on the elongate member.

16. The device of claim 15, in which the means for performing acoustic-to-optical transducing includes a user-selectable longitudinal location, and in which the profile of the device is less than 1 millimeter in diameter, and wherein the device has sufficient rigidity to permit introducing a separate ancillary device into the body using the device, and wherein the device is sized and shaped for being used for intravascular imaging in conjunction with catheterization, and in which the means for performing acoustic-to-optical transducing includes a Bragg grating.

17. The device of claim 16, further including a tunable laser, optically coupled to the Bragg grating sensor, the Bragg grating including a variable period, the laser operable to adjust an effective location of the Bragg grating sensor by adjusting a wavelength of light to select a desired portion of the Bragg grating sensor that provides a corresponding desired period.

18. A device comprising:
an elongate member including proximal and distal ends, and defining a longitudinal direction therebetween, the elongate member including an optical fiber extending along the longitudinal direction of the elongate member, wherein a distal portion of the elongate member is configured to be introduced into a human or animal body for internally imaging a portion of the body;
a strength member disposed about the elongate member, the strength member defining a plurality of apertures;
an acoustic transmitter on the distal portion of the elongate member that is configured to be introduced into a human or animal body for internally imaging a portion of the body; and
an acoustic-to-optical transducer at each of a plurality of separately addressable locations on different ones of the optical fibers and respectively corresponding to the plurality of apertures, the locations circumferentially distributed about a circumference of the elongate member and distributed along the optical fiber in the longitudinal direction, on the distal portion of the elongate member that is configured to be introduced into a human or animal body for internally imaging a portion of the body, wherein the separately addressable locations are configured to be selectively addressed by adjusting a wavelength of light, and wherein the plurality of separately addressable discrete locations are configured to be scanned for performing the imaging through the plurality of apertures.

19. The device of claim 18, wherein the separately addressable locations are spaced apart from each other.

20. The device of claim 18, wherein the elongate member includes a sufficiently small diameter and sufficient rigidity to permit use for introducing a separate ancillary device into the body.

21. The device of claim 18, wherein the acoustic-to-optical transducer includes a Bragg grating sensor.

22. The device of claim 21, wherein the Bragg grating includes a variable period for selectively addressing a location along the Bragg grating.

23. The device of claim 18, further comprising a tunable laser configured for selectively addressing by adjusting a wavelength of light provided by the laser.

24. A method comprising:
delivering acoustic energy to internal locations within a body using an elongate imaging device that includes proximal and distal ends defining a longitudinal direction therebetween, the elongate member including an optical fiber and a plurality separately addressable discrete locations of the optical fiber at different locations distributed about a circumference of the elongate member along the longitudinal direction;
adjusting a wavelength of light in the optical fiber to select a particular discrete location for delivering acoustic energy through a strength member disposed about the elongate imaging device and defining a plurality of apertures;
receiving, within the body, acoustic energy reflected from the body;
transducing, within the body, the received acoustic energy into an optical signal including circumferentially distributed imaging information; and
communicating the optical signal to a location outside of the body for forming a circumferentially distributed image.

25. The method of claim 24, comprising:
introducing a catheter over the elongate imaging device; and
guiding the catheter to a desired location using the elongate imaging device.

26. The method of claim 24, comprising:
introducing a stent over the elongate imaging device; and
positioning the stent at a desired location using the elongate imaging device.

27. The method of claim 24, in which the transducing includes using a Bragg grating.

* * * * *